United States Patent
Sudin et al.

(10) Patent No.: US 12,349,929 B2
(45) Date of Patent: Jul. 8, 2025

(54) SYSTEMS AND METHODS FOR INTRAVASCULAR OBSTRUCTION REMOVAL

(71) Applicant: RAPID MEDICAL LTD., Yokneam (IL)

(72) Inventors: Yuri Sudin, Modiin (IL); Aharon Friedman, Haifa (IL); Ronen Eckhouse, Shimshit (IL)

(73) Assignee: RAPID MEDICAL LTD., Yokneam (IL)

( * ) Notice: Subject to any disclaimer, the term of this patent is extended or adjusted under 35 U.S.C. 154(b) by 0 days.

(21) Appl. No.: 18/422,431

(22) Filed: Jan. 25, 2024

(65) Prior Publication Data
US 2024/0237999 A1 Jul. 18, 2024

Related U.S. Application Data

(63) Continuation of application No. 17/367,113, filed on Jul. 2, 2021, now Pat. No. 11,925,368, which is a
(Continued)

(51) Int. Cl.
*A61B 17/22* (2006.01)
*A61B 17/221* (2006.01)

(52) U.S. Cl.
CPC ...... *A61B 17/22031* (2013.01); *A61B 17/221* (2013.01); *A61B 2017/22001* (2013.01);
(Continued)

(58) Field of Classification Search
CPC ............ A61B 17/221; A61B 17/22031; A61B 17/32037; A61B 17/32031; A61B 17/320725; A61B 17/32012
See application file for complete search history.

(56) References Cited

U.S. PATENT DOCUMENTS

| | | | |
|---|---|---|---|
| 5,348,788 A | | 9/1994 | White |
| 6,066,149 A | * | 5/2000 | Samson ............... A61B 17/221 606/127 |

(Continued)

FOREIGN PATENT DOCUMENTS

| | | |
|---|---|---|
| CN | 102077870 A | 6/2011 |
| CN | 103764049 A | 4/2014 |

(Continued)

OTHER PUBLICATIONS

Examination Report No. 1 from IP Australia for counterpart Australian Application No. 2016214072, mailed Sep. 16, 2019 (3 pages).
(Continued)

*Primary Examiner* — Tuan V Nguyen
(74) *Attorney, Agent, or Firm* — The Roy Gross Law Firm, LLC; Roy D. Gross (57) ABSTRACT

Intraluminal devices and methods for removing an obstruction from a blood vessel using an intraluminal device are provided. The intraluminal device can include a flexible shaft and an expandable wire mesh structure extending from the flexible shaft, the wire mesh structure including at least one first expandable section having a first wire arrangement pattern and at least one second expandable section having a second wire arrangement pattern different from the first wire arrangement pattern. In addition, interstices in the at least one first expandable section can differ in size from interstices in the at least one second expandable section.

18 Claims, 11 Drawing Sheets

Related U.S. Application Data continuation of application No. 15/548,973, filed as application No. PCT/IB2016/000200 on Feb. 5, 2016, now Pat. No. 11,083,473.

(60) Provisional application No. 62/112,862, filed on Feb. 6, 2015.

(52) U.S. Cl.
CPC .............. *A61B 2017/22034* (2013.01); *A61B 2017/2212* (2013.01)

(56) References Cited

U.S. PATENT DOCUMENTS

| | | |
|---|---|---|
| 6,409,750 B1 | 6/2002 | Hyodoh et al. |
| 7,004,954 B1 | 2/2006 | Voss et al. |
| 8,795,305 B2 | 8/2014 | Martin et al. |
| 2005/0154400 A1 | 7/2005 | Kato et al. |
| 2006/0030933 A1 | 2/2006 | Delegge et al. |
| 2007/0135834 A1 | 1/2007 | Clubb et al. |
| 2007/0106302 A1 | 5/2007 | Ortiz |
| 2007/0106370 A1 | 5/2007 | Chouinard et al. |
| 2007/0168019 A1 | 7/2007 | Amplatz et al. |
| 2007/0185500 A1 | 8/2007 | Martin et al. |
| 2008/0262528 A1 | 10/2008 | Martin |
| 2009/0062841 A1 | 3/2009 | Amplatz et al. |
| 2011/0213403 A1 | 9/2011 | Aboytes |
| 2011/0245841 A1 | 10/2011 | Shohat et al. |
| 2012/0283510 A1 | 11/2012 | Alexander |
| 2013/0158592 A1 | 6/2013 | Porter |
| 2014/0046359 A1 | 2/2014 | Bowman et al. |
| 2014/0277098 A1 | 9/2014 | Janardhan et al. |
| 2014/0371779 A1 | 12/2014 | Vale et al. |
| 2015/0223829 A1 | 8/2015 | Aboytes |
| 2015/0374483 A1* | 12/2015 | Janardhan .......... B23K 26/1435 606/200 |

FOREIGN PATENT DOCUMENTS

| | | |
|---|---|---|
| CN | 104168845 A | 11/2014 |
| JP | H 10-151136 A | 6/1998 |
| JP | 2003-513748 A | 4/2003 |
| WO | WO 2011/106426 A1 | 9/2011 |
| WO | WO 2013/005195 | 1/2013 |
| WO | WO 2013/102848 A2 | 7/2013 |
| WO | WO 2014/081077 A1 | 5/2014 |

OTHER PUBLICATIONS

Office Action from the Japan Patent Office for counterpart Japanese Application No. 2017-541338, mailed Nov. 26, 2019, with translation (13 pages).

First Notification of Office Action issued by the China National Intellectual Property Administration on Nov. 27, 2019, in corresponding Chinese Application No. 201680008197.0.

Extended European Search Report dated Nov. 9, 2018, issued by the European Patent Office in counterpart European Patent Application No. EP 16 74 6182.1.

International Search Report from the U.S. Patent & Trademark Office for International Application No. PCT/IB2016/000200, mailing date Aug. 5, 2016.

Written Opinion of the International Searching Authority from the U.S. Patent & Trademark Office for International Application No. PCT/IB2016/000200, mailing date Aug. 5, 2016.

Israel Office Action in counterpart application 1253581 dated Sep. 30, 2021 (11 pages).

Chinese Office Action in counterpart application 201680008197.0 dated Aug. 12, 2021 (17 pages).

\* cited by examiner

SYSTEMS AND METHODS FOR INTRAVASCULAR OBSTRUCTION REMOVAL

PRIORITY

This application is a continuation of U.S. application Ser. No. 17/367,113, filed Jul. 2, 2021, which is a continuation of U.S. application Ser. No. 15/548,973, filed Aug. 4, 2017 (issued as U.S. Pat. No. 11,083,473 on Aug. 10, 2021), which is a National Stage Entry of PCT/IB2016/000200, filed Feb. 5, 2016, which claims the benefit of priority from U.S. Provisional Application No. 62/112,862 filed Feb. 6, 2015, the disclosures of each of which are herein incorporated by reference in their entirety.

FIELD

This disclosure relates to intravascular and/or intraluminal medical devices and systems that are configured to retrieve an obstruction from human blood vessels. The disclosure also relates to methods of removing an obstruction from human blood vessels.

SUMMARY

This disclosure describes an intravascular and/or intraluminal medical device that may retrieve an obstruction from human blood vessels. This obstruction may be a blood clot (of embolic or thrombotic origin). The device may be constructed from an expandable mesh structure extending from an elongated shaft. The expandable mesh structure may utilize differing wire arrangement patterns to create a structure with variable interstices sizes and/or one or more expandable sections. As a result, when the device is expanded alongside or within a clot inside a blood vessel, the clot may penetrate the mesh due to the large interstices, and then when the mesh is retrieved, the clot may be held in the mesh. In other words, when the mesh applies radial forces on the clot, it may present large enough openings to expand through the clot. In some embodiments, when the expanded mesh applies axial forces on the clot, it may present small enough openings to hold the clot during clot retrieval. The wire arrangement patterns might be such that the interstices in the distal and proximal ends of the mesh may be smaller than at least some of the interstices that are more central. However, other arrangement patterns might also be used. For instance, the device may be made out of only two types of wire arrangement patterns, the distal one with relatively smaller openings or interstices and the proximal one with relatively larger openings or interstices.

BRIEF DESCRIPTION OF THE DRAWINGS

The accompanying drawings, which are incorporated in and constitute a part of this specification, illustrate embodiments and, together with the description, serve to explain the features, advantages, and principles of the disclosed embodiments.

DESCRIPTION OF EXEMPLARY EMBODIMENTS

Reference will now be made in detail to the one or more embodiments, characteristics of which are illustrated in the accompanying drawings. Wherever possible, the same reference numbers will be used throughout the drawings to refer to the same or like parts.

Figure 1:
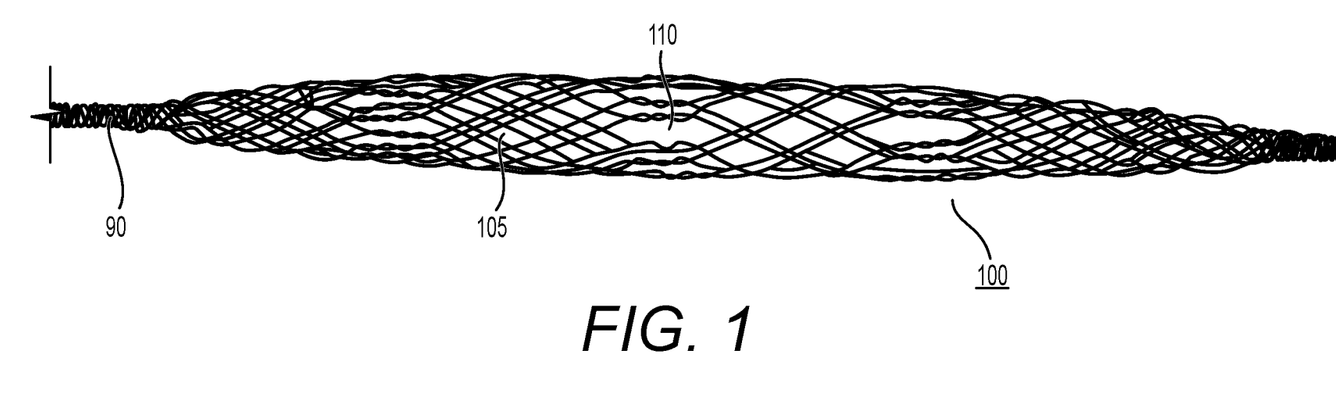
FIG. 1 depicts an expandable mesh structure with varying wire arrangements creating interstices of different sizes consistent with the disclosure.

FIG. 1 depicts a mesh structure associated with expandable mesh structure 100. The mesh structure depicted in FIG. 1 includes with varying wire arrangements, which can create interstices of different sizes when the expandable mesh structure 100 is in an expanded state. For example, interstices 110 in expandable mesh structure 100 can be larger than interstices 105 in expandable mesh structure 100 when expandable member 100 is in an expanded state. In addition, the wires of the expandable mesh structure 100 can be used to create a cable shaft, such as cable shaft 90.

In some embodiments, the interstices in a first expandable section may differ in size from the interstices in a second expandable section by a predetermined amount. For example, the interstices in the second expandable section may be approximately three times, five times, ten times, or twenty times larger than the interstices in the first expandable section.

Figure 2:
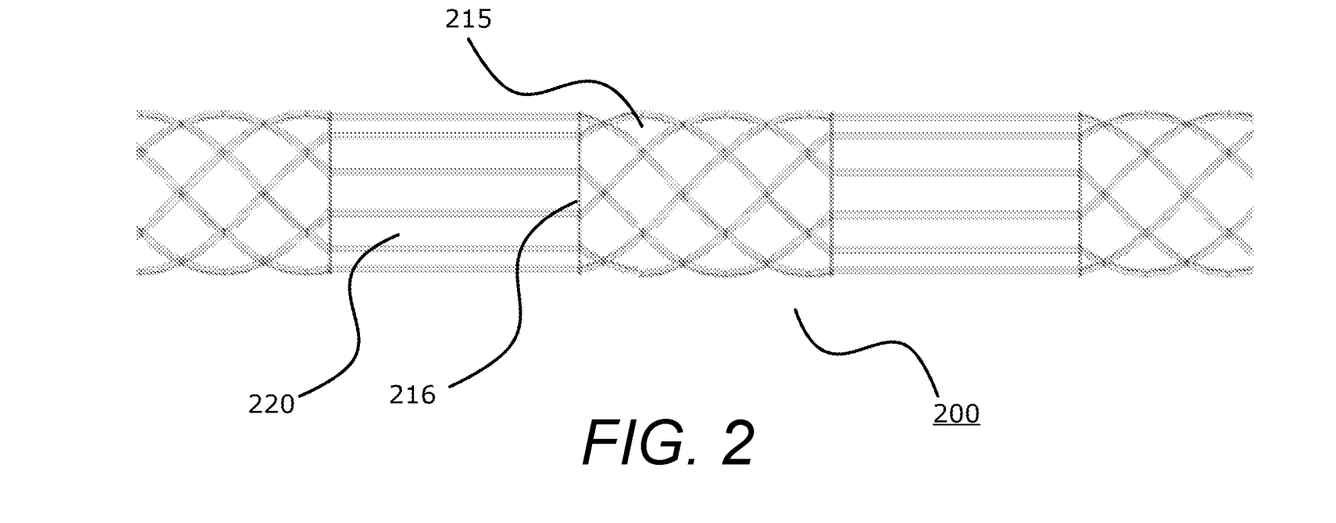
FIG. 2 depicts an alternative mesh arrangements of braiding and straight wires consistent with the disclosure.

It should be noted that this invention is not limited to a device with only two wire arrangements; alternating wire arrangements can also be used to create a structure with varying sized openings. For instance, one embodiment of the device can be made of alternating braided wires and a segment of straight or non-braided wires (FIG. 2). In this structure, the braided portion between the straight wire segments may be a stable piece that holds the wire arrangements together. In addition, it may create a border between the large openings. Specifically, FIG. 2 depicts expandable mesh structure 200 with alternative mesh arrangements. For example, region 215 of expandable mesh structure 200 can include braided wires and region 220 of expandable mesh structure 200 can include straight (or aligned, parallel) wires.

Figure 3:
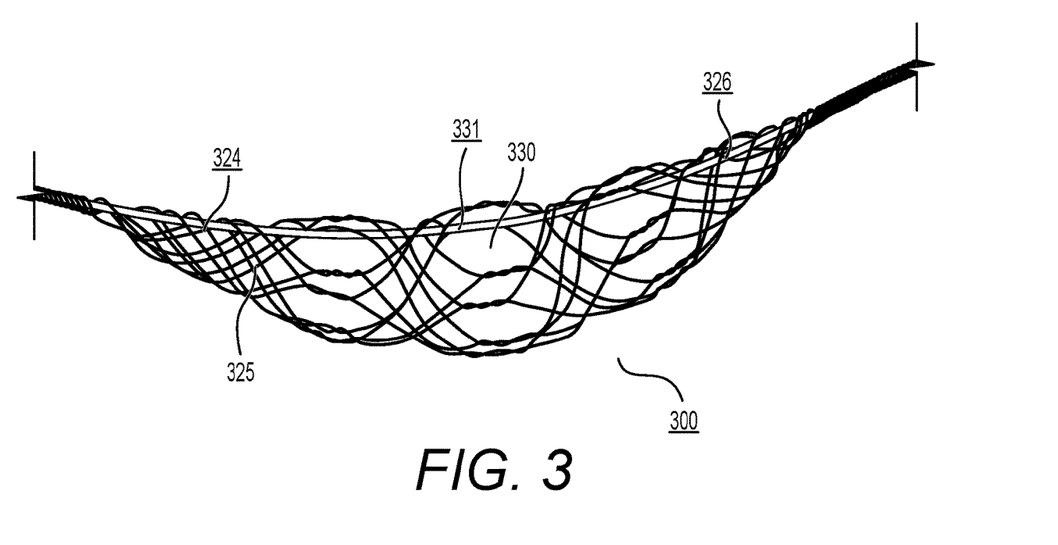
FIG. 3 depicts an expandable mesh structure with alternating braided and intertwined wire couples consistent with the disclosure.

In yet another embodiment, a plurality of wires in the large interstices section can be intertwined to create even larger openings. FIG. 3 is an illustration of an expandable mesh structure 300 in which each couple of wires is intertwined between the braided sections and, as a result, the large openings are created. In this embodiment, the distal braided section also serves as a filter in case particles break off and flow distally during the retrieval process. Specifically, in the embodiment depicted in FIG. 3, expandable mesh structure 300 is shown with a braided region 324 that transitions to an intertwined region 331 (with intertwined wire couples), and then is shown as transitioning (or alternating) back to a braided region 326. The interstices 325 can be smaller than the interstices 330 when expandable mesh structure 300 is in an expanded state.

Figure 4:
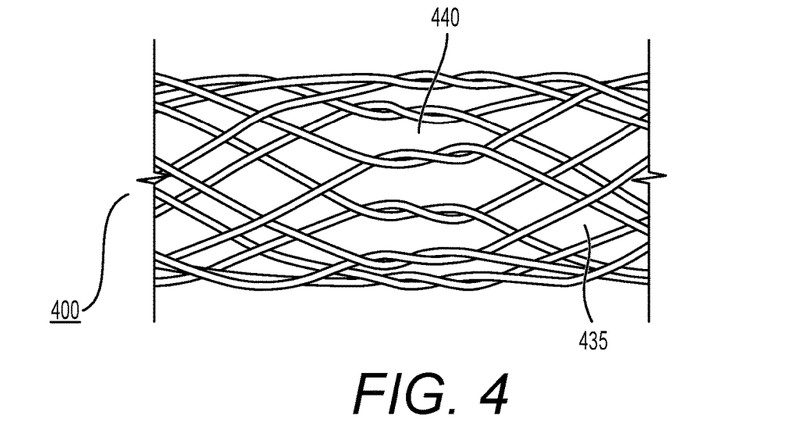
FIG. 4 depicts an expanded view of an intertwined section consistent with the disclosure which creates larges interstices.

FIG. 4 depicts a close-up view of expandable mesh structure 400 (when in an expanded state). As shown in FIG. 4, interstices 440 (associated with a region of intertwined wires) can be larger than interstices 435 (associated with a braided arrangement).

Figure 5:
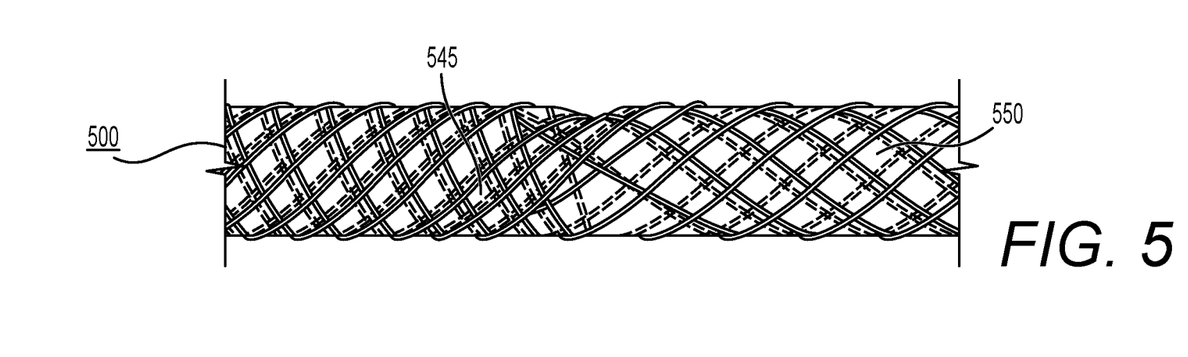
FIG. 5 illustrates a 1×1 braiding arrangement that transitions to a 1×3 braiding arrangement consistent with the disclosure.
Figure 6:
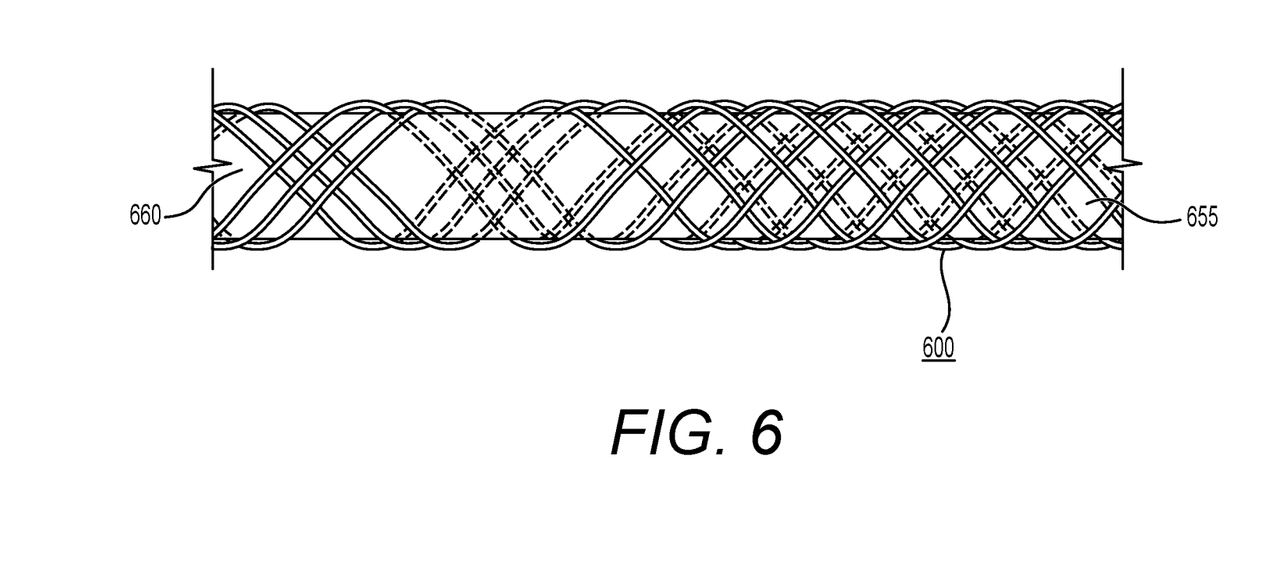
FIG. 6 illustrates another braiding arrangement consistent with the disclosure.

Furthermore, other braiding patterns can be utilized to create the different interstices. For example, 1×1 (one wire over one wire) can be used for the small dense section and 3×1 (3 wires over 1 wire) can be used in the larger interstices section (FIG. 5). Other braiding examples are, but are not limited to, 2×2 (two wires over two wires) combined with three intertwined wires, or 2×2 combined with 4×1 or 1×1 combined with 3×3 (FIG. 6).

More specifically, FIG. 5 depicts an expandable mesh structure 500 which includes a 1×1 braiding arrangement (in region 545) that transitions to a 1×3 braiding arrangement (in region 550). As shown in FIG. 5, the interstices in region 550 can be larger than the interstices in region 545. FIG. 6 depicts an expandable mesh structure 600 which includes a 1×1 braiding arrangement throughout; however the interstices in region 660 can be larger than the interstices in region 655 when expandable mesh structure 600 is in an expanded state.

Figures 7A, 7B:
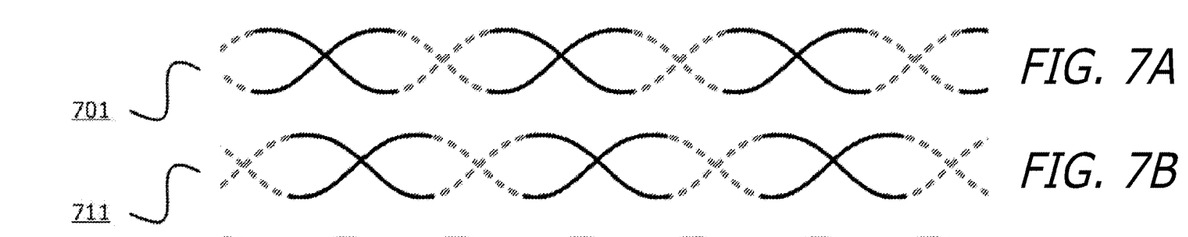
FIGS. 7A-7F illustrate the components of a braiding arrangement with uniform interstices.
Figures 7C, 7D, 7E, 7F:
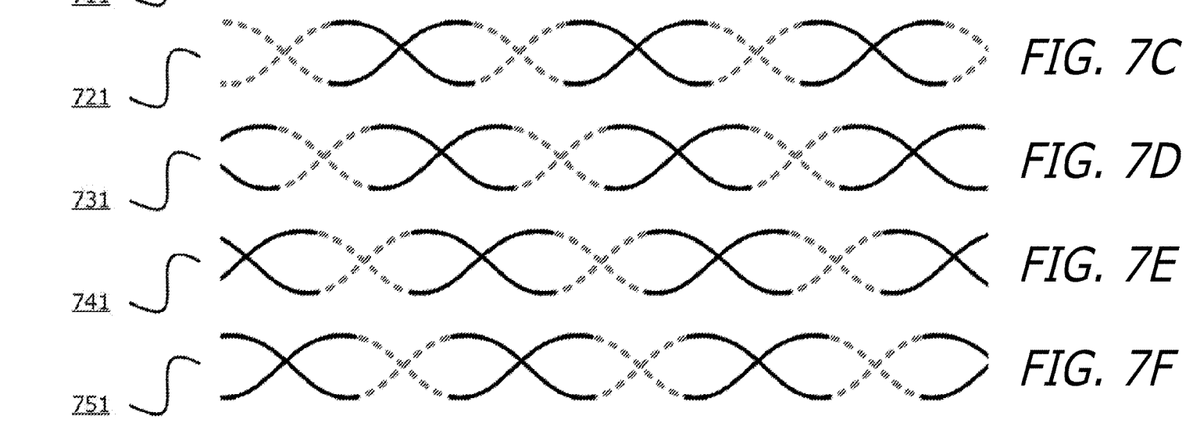
Figure 7G:
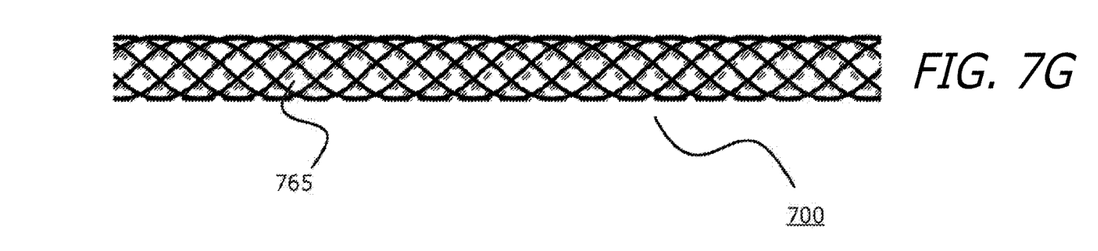
FIG. 7G illustrates the combined components of FIGS. 7A-7F.

FIG. 7 depicts pairs of continuous braided wires (pair 701 in FIG. 7A, pair 711 in FIG. 7B, pair 721 in FIG. 7C, pair 731 in FIG. 7D, pair 741 in FIG. 7E, and pair 751 in FIG. 7F) that, together, make up the braid with uniform interstices 765 depicted in expandable mesh structure 700 (FIG. 7G). In an expanded state, the expandable mesh structure 700 includes a hollow region (shown as cylindrical in FIG. 7). The dashed lines in FIG. 7 (and in FIGS. 8-12) correspond to that portion of a continuous wire that falls "behind" the hollow portion (when viewed from the "front" as shown in FIG. 7).

Figure 8A:
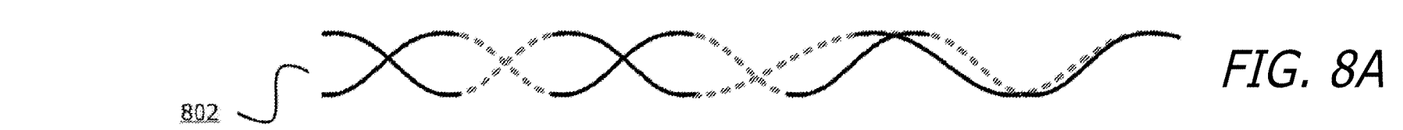
FIGS. 8A-8F illustrate the components of 1×1 braiding arrangement that transitions to a 1×3 braiding arrangement consistent with the disclosure.
Figures 8B, 8C:
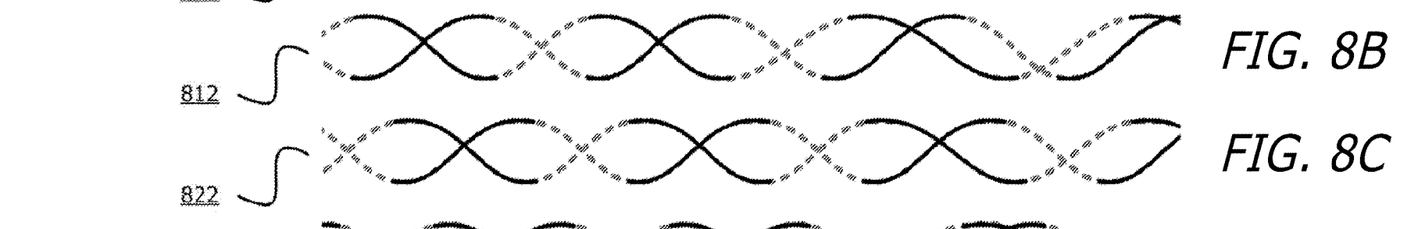
Figures 8D, 8E:
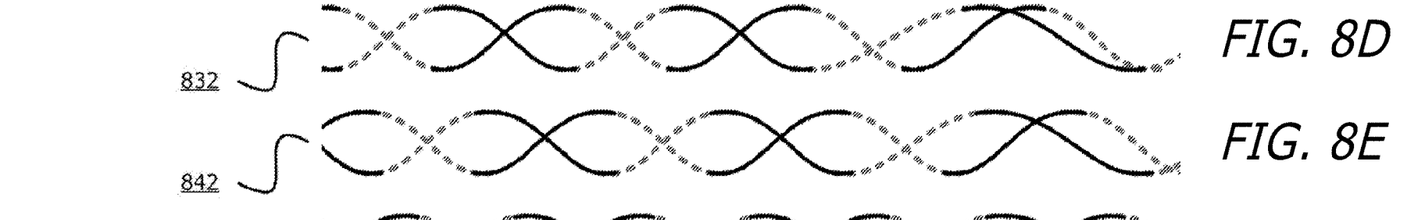
Figure 8F:
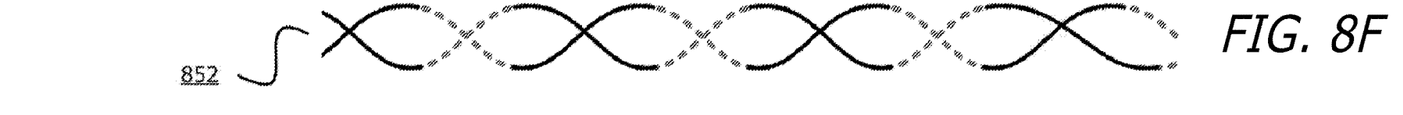
Figure 8G:
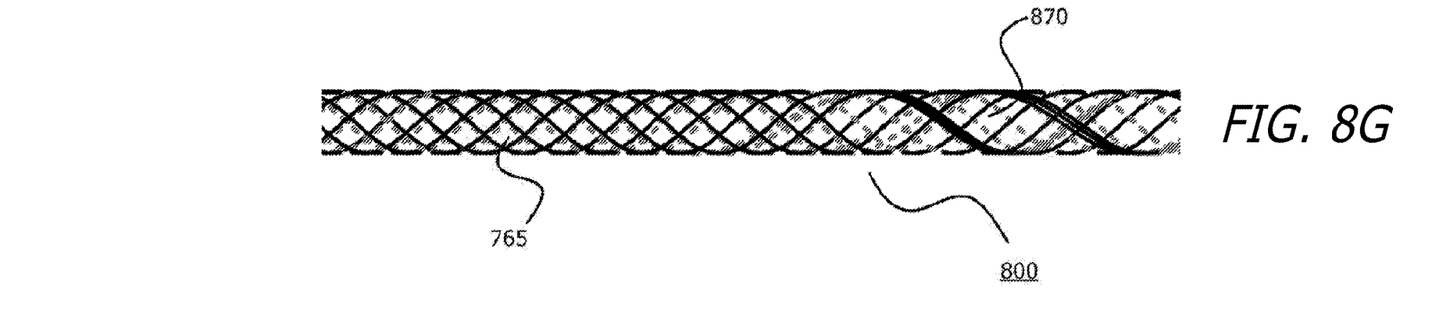
FIG. 8G illustrates the combined components of FIGS. 8A-8F.

FIG. 8 depicts pairs of continuous braided wires (pair 802 in FIG. 8A, pair 812 in FIG. 8B, pair 822 in FIG. 8C, pair 832 in FIG. 8D, pair 842 in FIG. 8E, and pair 852 in FIG. 8F) that, together, make up the 1×1 braiding arrangement that transitions to a 1×3 braiding arrangement depicted in the expandable mesh structure 800 of FIG. 8G. As shown in FIG. 8G, interstices 870 can be larger than interstices 765 when expandable mesh structure 800 is in an expanded state.

Figure 9A:
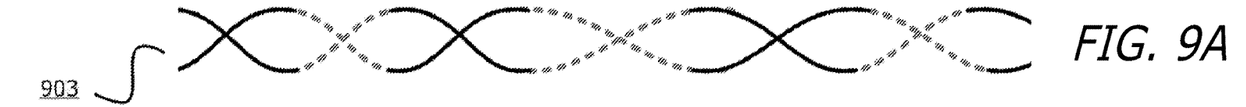
FIGS. 9A-9F illustrate the components of 1×1 braiding arrangement that transitions to a 3×3 braiding arrangement consistent with the disclosure.
Figure 9B:
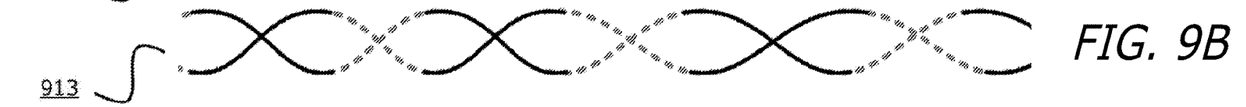
Figure 9C:
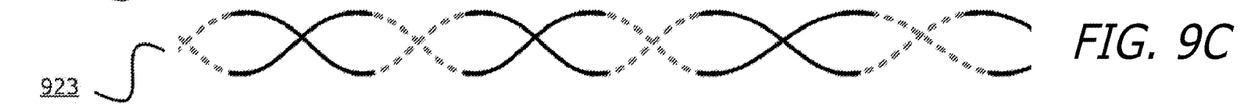
Figure 9D:
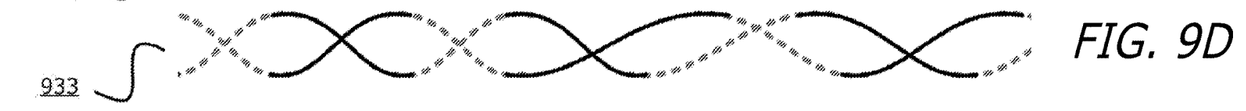
Figure 9E:
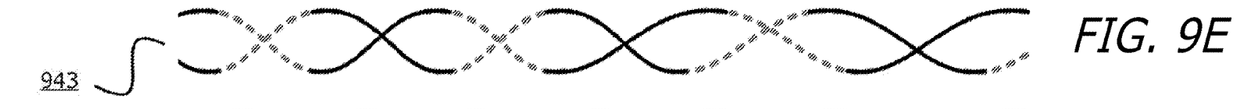
Figure 9F:
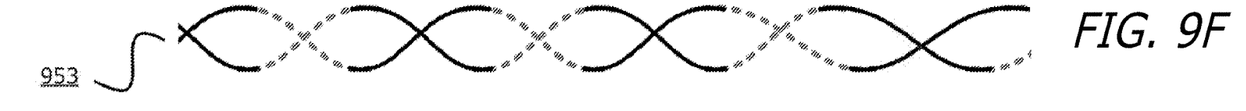
Figure 9G:
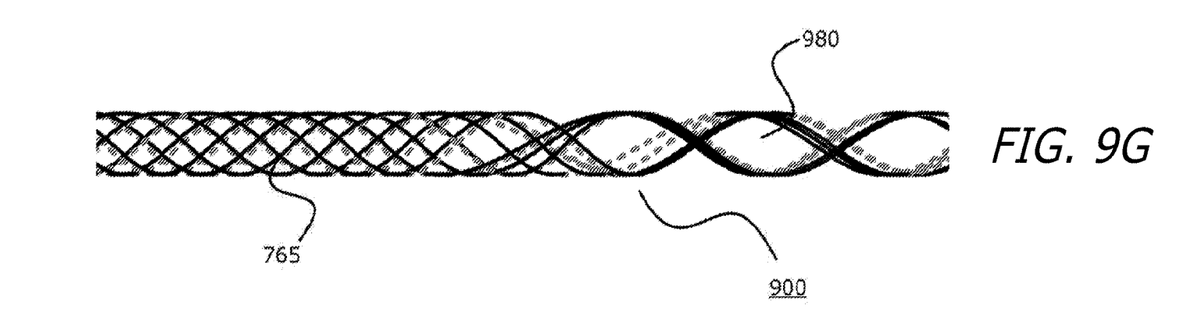
FIG. 9G illustrates the combined components of FIGS. 9A-9F.

FIG. 9 depicts pairs of continuous braided wires (pair 901 in FIG. 9A, pair 913 in FIG. 9B, pair 923 in FIG. 9C, pair 933 in FIG. 9D, pair 943 in FIG. 9E, and pair 953 in FIG. 9F) that, together, make up the 1×1 braiding arrangement that transitions to a 3×3 braiding arrangement depicted in the expandable mesh structure 900 of FIG. 9G. As shown in FIG. 9G, interstices 980 can be larger than interstices 765 when expandable mesh structure 900 is in an expanded state.

Figure 10A:
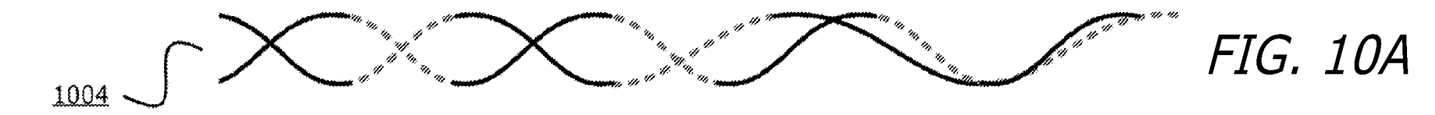
FIGS. 10A-10D illustrate the components of 1×1 braiding arrangement that transitions to a 1×2 braiding arrangement consistent with the disclosure.
Figure 10B:
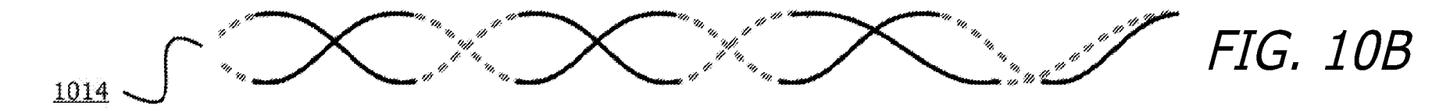
Figure 10C:
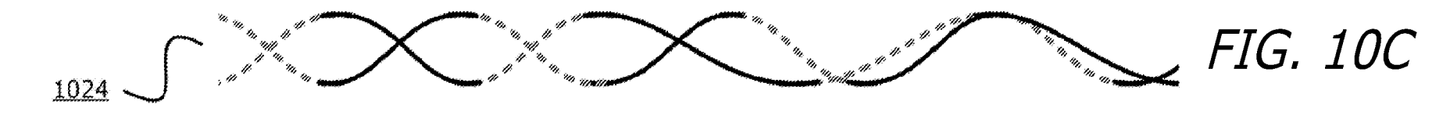
Figure 10D:
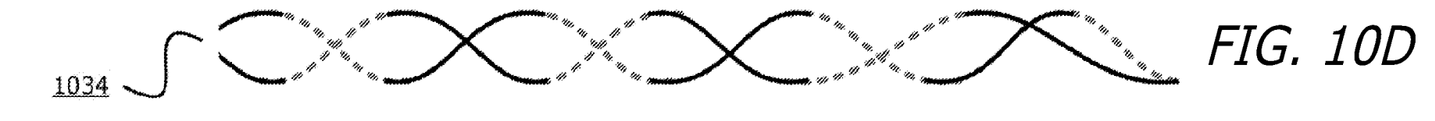
Figure 10E:
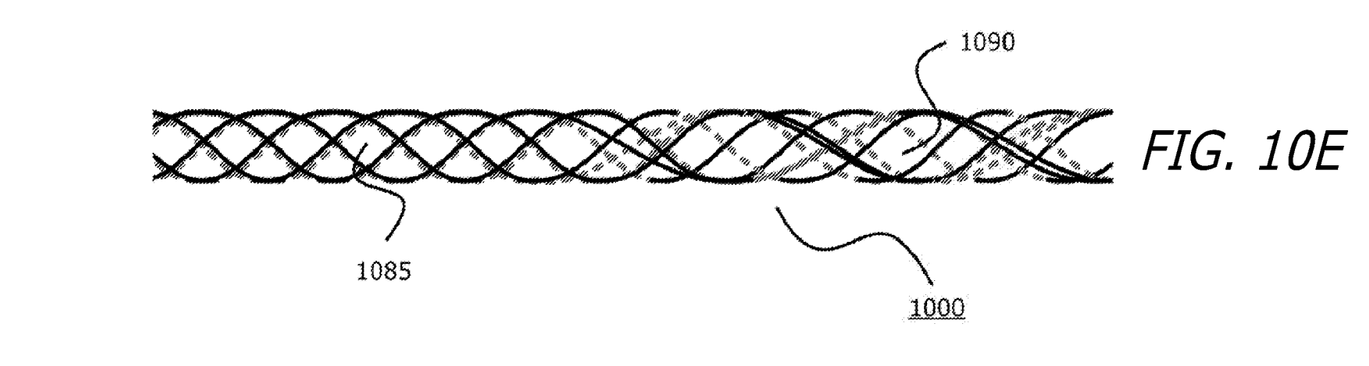
FIG. 10E illustrates the combined components of FIGS. 10A-10D.

FIG. 10 depicts pairs of continuous braided wires (pair 1004 in FIG. 10A, pair 1014 in FIG. 10B, pair 1024 in FIG. 10C, and pair 1034 in FIG. 10D) that, together, make up the 1×1 braiding arrangement that transitions to a 1×2 braiding arrangement depicted in the expandable mesh structure 1000 of FIG. 10E. As shown in FIG. 10E, interstices 1090 can be larger than interstices 1085 when expandable mesh structure 1000 is in an expanded state.

Figure 11A:
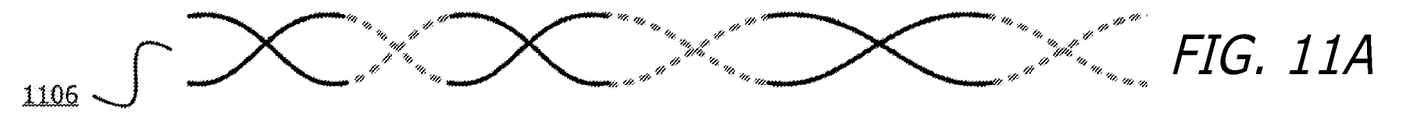
FIGS. 11A-11D illustrate the components of 1×1 braiding arrangement that transitions to a 2×2 braiding arrangement consistent with the disclosure.
Figure 11B:
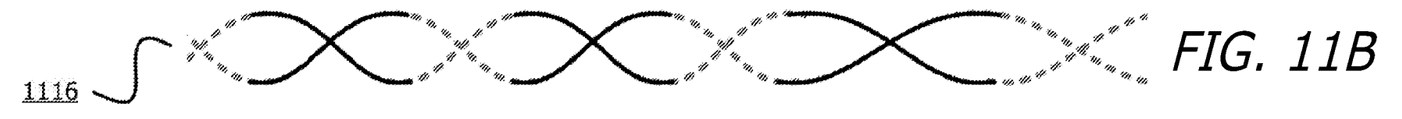
Figure 11C:
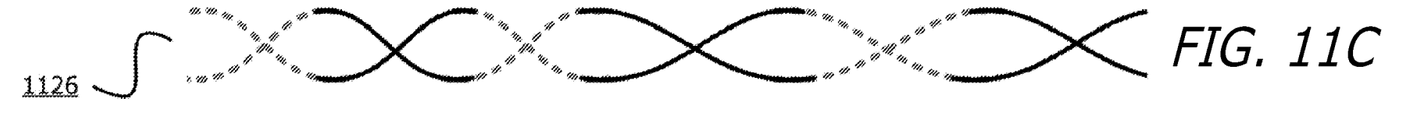
Figure 11D:
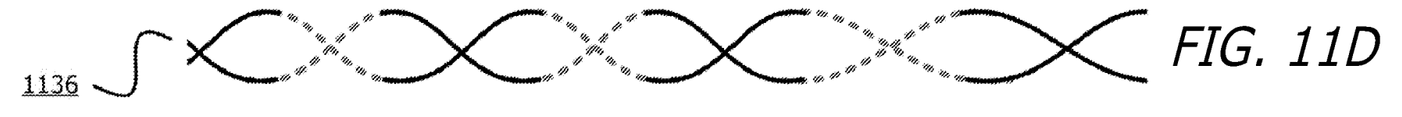
Figure 11E:
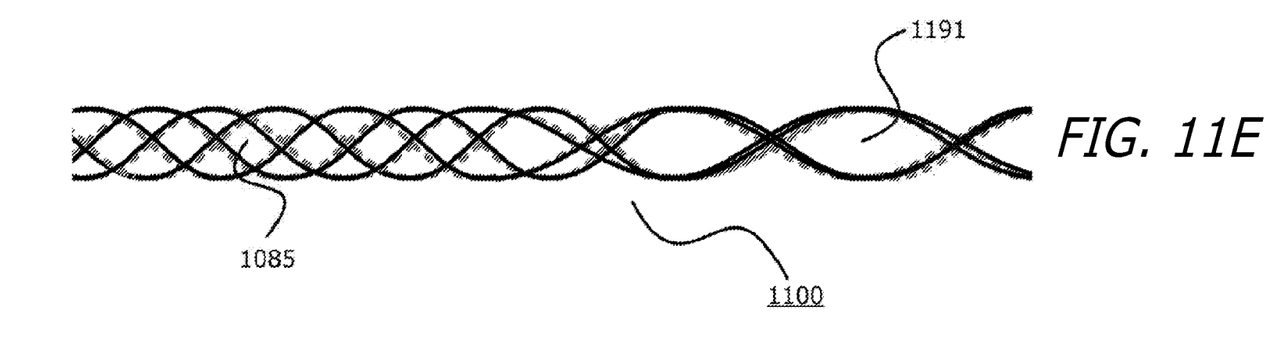
FIG. 11E illustrates the combined components of FIGS. 11A-11D.

FIG. 11 depicts pairs of continuous braided wires (pair 1106 in FIG. 11A, pair 1116 in FIG. 11B, pair 1126 in FIG. 11C, and pair 1136 in FIG. 11D) that, together, make up the 1×1 braiding arrangement that transitions to a 2×2 braiding arrangement depicted in the expandable mesh structure 1100 of FIG. 11E. As shown in FIG. 11E, interstices 1191 can be larger than interstices 1085 when expandable mesh structure 1100 is in an expanded state.

Figure 12A:
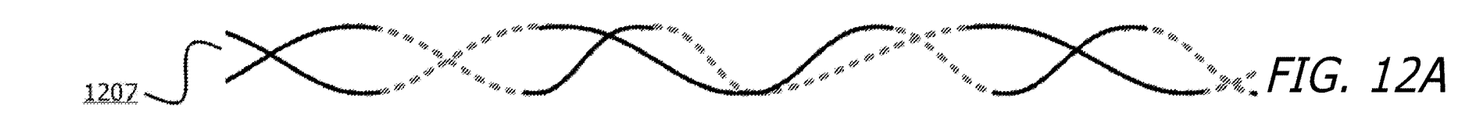
FIGS. 12A-12D illustrate the components of 2×2 braiding arrangement that transitions to a 1×4 braiding arrangement consistent with the disclosure.
Figure 12B:
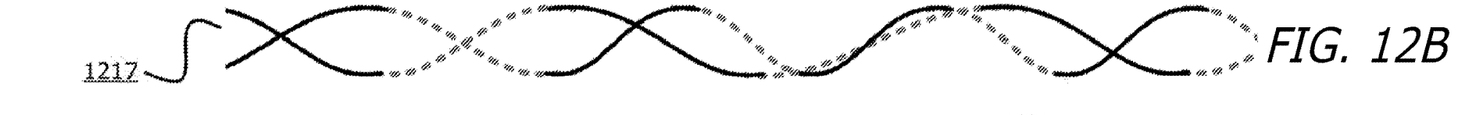
Figure 12C:
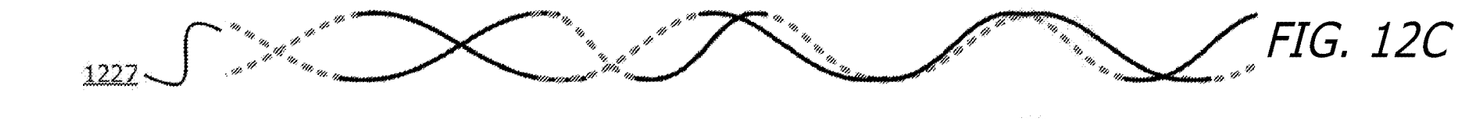
Figure 12D:
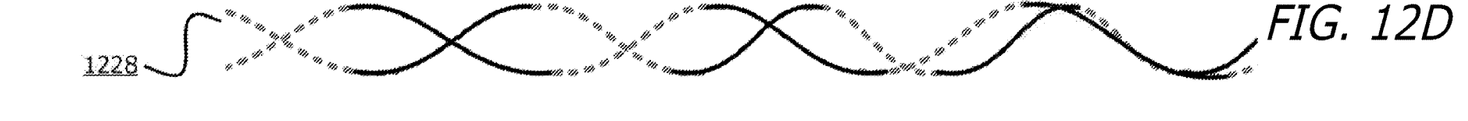
Figure 12E:
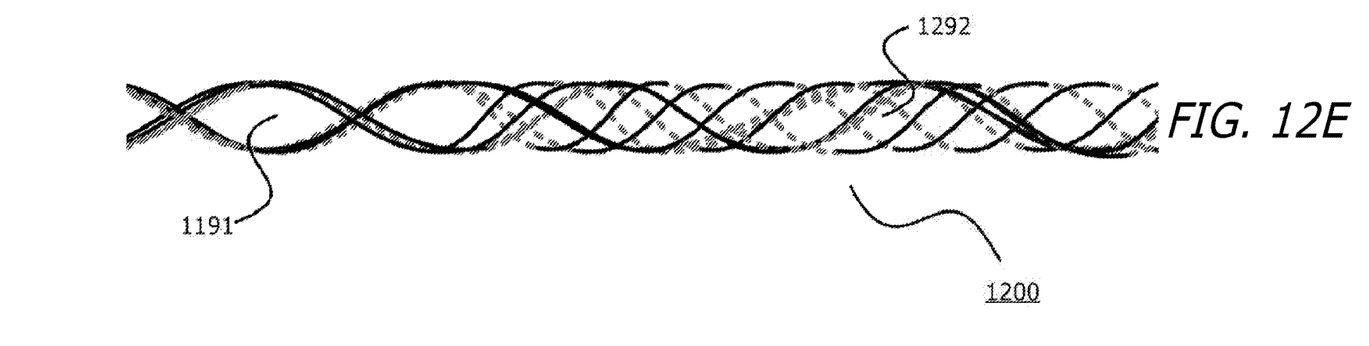
FIG. 12E illustrates the combined components of FIGS. 12A-12D.

FIG. 12 depicts pairs of continuous braided wires (pair 1207 in FIG. 12A, pair 1217 in FIG. 12B, pair 1227 in FIG. 12C, and pair 1237 in FIG. 12D) that, together, make up the 2×2 braiding arrangement that transitions to a 1×4 braiding arrangement depicted in the expandable mesh structure 1200 of FIG. 12E. As shown in FIG. 12E, interstices 1191 can be larger than interstices 1292 when expandable mesh structure 1200 is in an expanded state.

In yet another embodiment, the larger interstices can be created by keeping the same general wire arrangements (for instance one over one) but by changing the angle of the intersection. In yet another option, the large interstices can be achieved by reducing the number of wires at some portion of the arrangement (for instance, by terminating a number of the wires at the end of the first section).

Further, in some embodiments, each of the expandable sections may be configured to expand to different outer diameters. For example, a first expandable section may be configured to expand to an outer diameter smaller than the outer diameter of the second expandable section when the second expandable section is expanded. That is, when each of the sections of the device is expanded, the device may have multiple, different outer diameters along the length of the device.

Additionally, the expandable sections having different expanded outer diameters may be arranged in any desired order with respect to one another along the length of the device. For example, in one embodiment, a first type of expandable section may be located between a plurality of expandable sections of a second type. This arrangement may result in an expandable structure with at least two peaks and one valley. However, other arrangements may result in an expandable structure with other quantities of peaks and valleys formed as a result of the different diameters of the expandable sections. By way of example only, there may be three valleys and two peaks, or four valleys and three peaks. More generally, there may be one more valley than there are peaks. Or there could be an equal number of peaks and valleys. Or, there could be one more peak than there are valleys.

Moreover, the single wires can differ from each other in their characteristics; material, diameter, shape, cross-sectional shape, radio-opacity, etc. For instance, one Platinum wire can be used to make the structure visible under fluoroscopy while the other wires can be of less visible materials, such as Nitinol. In different embodiments, polymer wires can be combined with metal wires to achieve the required mechanical properties of the structure. In addition, flat wire might be used to lower the overall profile of the device or round wires can be used for better kink resistance. Nonetheless, the disclosure above can incorporate any types of wires from any materials, sizes and shapes. In addition, the wires might be coated or covered. A coating might be desirable to ease the delivery of the structure through a tight micro-catheter. In addition, the wires might be drug coated to affect a treatment or to increase adherence to the clot. Finally, the section of the small interstices might be covered with an outer polymer or other covering to allow even greater protection against distal shower.

Figure 13:
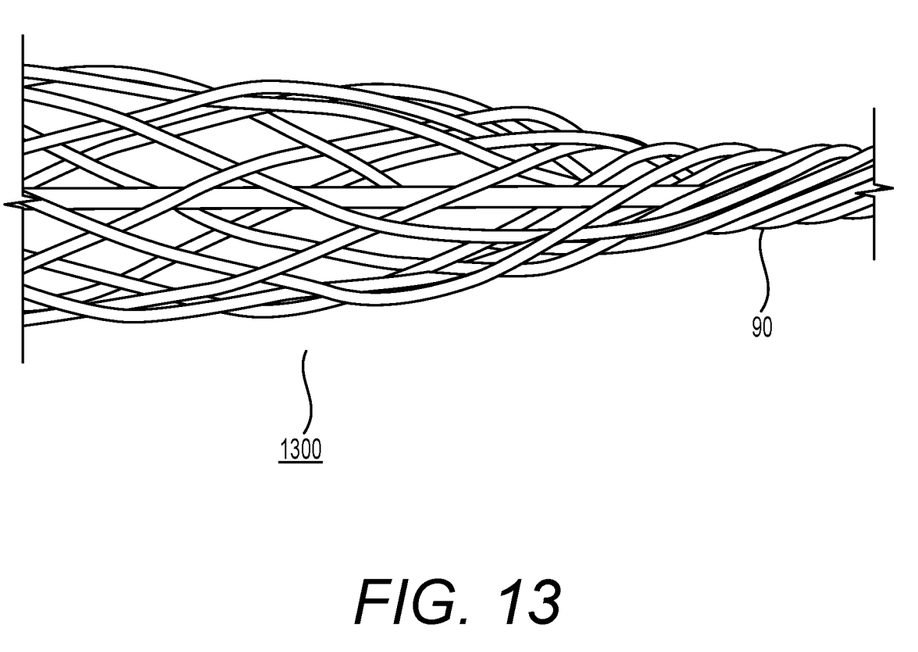
FIG. 13 illustrates an expandable mesh created from wires of a cabled shaft consistent with the disclosure.

The expandable mesh may also be extended from an elongate shaft. The shaft may be long enough to deliver and control the mesh from outside the body. The shaft might be made of a stiff portion to enhance pushability and stability on its proximal part, and a flexible portion on its distal part. The distal part may be connected at its distal end to the expandable mesh. The proximal stiffer part can be produced from a hollow metallic tube or from a reinforced polymer structure. The distal and/or proximal part might be also created from a reinforced polymer structure of a more flexible nature. In addition, it might be created from a cut metallic tube. Moreover, it may be created like a cable, for example, from strands of wires arranged in a coiled assembly. If the latter cable-like assembly is utilized, the wires of the cables can also be used to create the expandable mesh structure. In this case, a bond between the shaft and the expandable portion may not be necessary. As a result, the device can be made very flexible, thus simplifying the assembly process (FIG. 13). Specifically, FIG. 13 illustrates expandable mesh 1300 created from wires of a cabled shaft (such as shaft 90).

There are different ways to expand the expandable mesh member that is extended from the shaft described above. One possibility is to make it self-expanding by setting its structure in the expanded shape. This can be achieved via heat treatment if the device is made of metallic wires such as Nitinol.

Another alternative is to use one or more pull or control wires that can be connected to the expandable members. These wires may extend through the flexible portion of the shaft to the proximal portion of the shaft and, when a force is exerted on the pull or control wire (e.g., a pull force), the mesh member may expand. In one embodiment, only one core wire may be used and connected to the expandable member at its distal end. In this case, the wires of the expandable member might terminate in a coiled structure. The pull wire may be connected to the coiled structure at the distal part of the expandable member. When the pull wire is pulled, it may expand all of the wires of the expandable member and thereby expanding the expandable member. In addition, the wires of the expandable member can terminate in other fashions. For example, they can be arranged in parallel at the distal end. In yet another embodiment, one or more of the wires can be curved back and used as pull wires themselves.

In some embodiments, the pull wire alternative may have some advantages over the self-expanding one. First, the amount of expansion might be controlled by use (the more pulled, the more expansion at the distal end) unlike the self-expanding option which may be pre-set. This can be beneficial if, for example, the clot is retrieved through blood vessels of varying diameter. In addition, since the device may be delivered in an unexpanded state, delivery through a tight micro-catheter might be easier. Yet an additional alternative for expansion of the expandable member is to use temperature changes or to utilize currents that will cause metallic wires to change their mechanical properties.

As mentioned above, the device disclosed may be used to remove an obstruction from a vessel. This obstruction may be a blood clot of different origins but is not limited to such. For instance, the obstruction can also be plaque of foreign bodies. Or the device may be sized for use in a conduit other than a blood vessel.

One embodiment of a method for removing an obstruction from a vessel with the disclosed device may include inserting the device having the expandable structure into the vessel. The expandable section may include at least one end region having interstices that are at least three times smaller in size than interstices in a central region. The expandable structure may then be positioned in a desired location. For example, the expandable structure may be moved so that at least the central region that coincides with the obstruction (e.g., is aligned with, alongside, fully within, or partially within the obstruction). Once aligned, the expandable structure may be expanded, for example, by using the pull or control wire, to embed some or all of the obstruction in the central region. The expandable structure containing the embedded obstruction may then be withdrawn from the vessel.

Figure 14A:
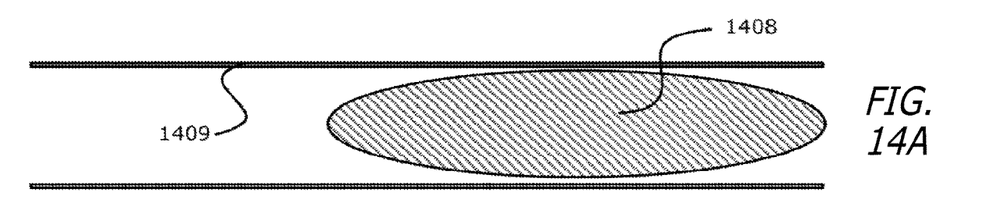
FIGS. 14A-14E illustrate a clot retrieval process consistent with the disclosure.
Figure 14B:
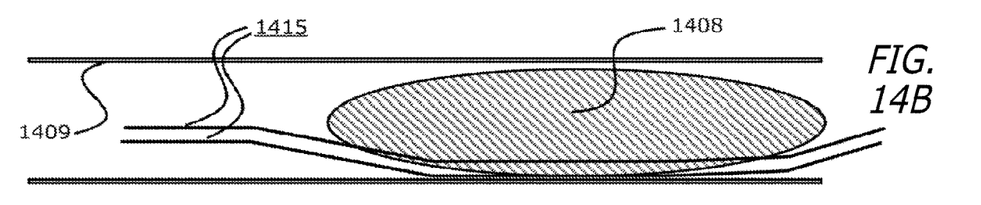
Figure 14C:
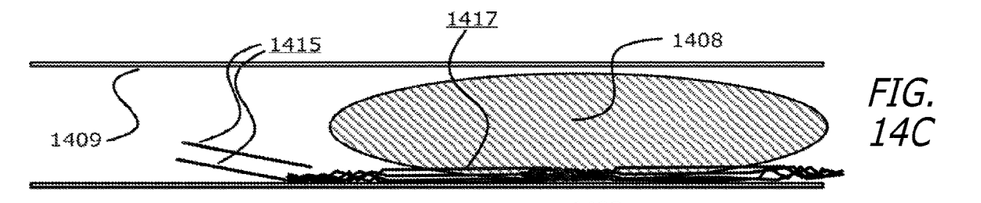

One implementation of the embodiment of the method for removing the obstruction from the vessel is illustrated in FIG. 14. However, it should be noted that while the method is illustrated in the context of clot removal from brain blood vessels, in other embodiments, the device may be used to remove a variety of other types of obstructions as well. In one embodiment, the method of use for the device may include one or more of the following:

1) The clot location may be identified using imaging. For example, FIG. 14A depicts clot 1408 in blood vessel 1409, where clot 1408 obstructs blood flow.
2) Using minimally invasive catheterization techniques, an 8 Fr guide catheter may be placed at the internal carotid artery.
3) A 3 Fr micro-catheter guided by a guidewire may be placed across the clot (the micro-catheter tip may be distally located with respect to the clot). As shown in FIG. 14B, micro-catheter 1415 can be advanced into blood vessel 1409 to the location of clot 1408 such that the opening of micro-catheter 1415 is on the distal side of clot 1408.
4) The guidewire may be removed while the micro-catheter remains in place.
5) The expandable member may be advanced through the micro-catheter. The shaft may be used to advance the expandable mesh to the micro-catheter tip. For example, an expandable member 1417 (in an unexpanded state) can be delivered through micro-catheter 1415 as shown in FIG. 14C to clot 1408.
6) The micro-catheter may be pulled back while the expandable member remains in place (its tip distal to the clot) and, as a result, the expandable member may be unsheathed alongside the clot.

Figure 14D:
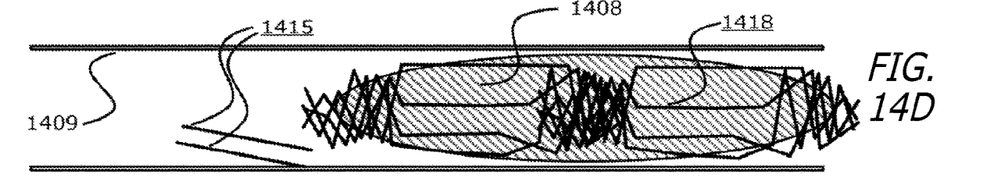

7) The pull wire may be pulled to expand the expandable member. The user may choose the amount of expansion necessary to penetrate the clot. For example, expandable member 1417 can be expanded though clot 1408 as shown in FIG. 14D.

8) The balloon guide catheter may be inflated, and the guide catheter may be aspirated to reverse the blood flow.

Figure 14E:
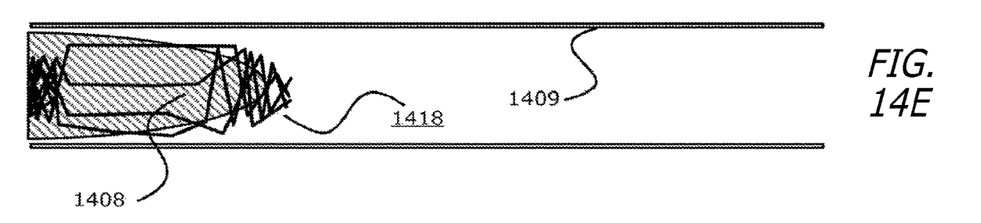

9) Both micro-catheter and the expandable member may be retrieved. The user might need to expand the expandable member when the device is pulled through larger vessels. The expandable member and micro-catheter may be retrieved through the guide catheter. As shown in FIG. 14E, expandable member 1417 and clot 1408 can then be retrieved.

In addition to the method of use described above, the expandable member can also be used to retrieve additional foreign materials from the bodily lumens. For example, it can also be used to retrieve pulmonary embolism, kidney stones, etc.

Further, in some embodiments, the device may include a flexible shaft made of 12 wires. In such embodiments, 6 of the wires may be arranged in a clockwise direction, and the other 6 may be arranged in a counterclockwise direction.

In some embodiments, the non-braided section of the expandable member may include intertwined pairs.

In some embodiments, the wires substantially do not cross in the non-braided section of the expandable member.

In some embodiments, different types of braiding may be employed in same expandable member.

The following terminology descriptions are exemplary, and not restrictive of embodiments of the invention, as described above.

An intraluminal device (or intraluminal expandable member) includes any expandable member that may be inserted into a lumen, conduit, or vessel.

A wire mesh structure includes any structure made at least wholly or partially from wire, regardless of whether the structure is made from metal, polymers, or any other material.

A wire arrangement pattern is a configuration of wires. In its broadest sense, the pattern does not have to have any measure of regularity. In some embodiments, the configuration may include repetition, in others there may be no repetition.

Interstices include any intervening space, including, for example, any form of gap, space, hole, interval, or slit.

A braid is a configuration of a plurality of strands with diagonal overlaying or overlap, such as in a weave or interlacing.

What is claimed is:

1. An intraluminal device, comprising:
    a flexible shaft;
    an expandable wire mesh structure extending from the flexible shaft, the expandable wire mesh structure including wires comprising a 1×2 braiding arrangement; and
    a control wire extending through the flexible shaft and the expandable wire mesh structure, wherein the expandable wire mesh structure is configured to expand when a force is exerted on the control wire;
    wherein at least a portion of the expandable wire mesh structure comprises alternating braided wires and intertwined wires.

2. The intraluminal device of claim 1, wherein the wires of the expandable wire mesh structure form intertwined wire couples between braided wires of the 1×2 braiding arrangement.

3. The intraluminal device of claim 1, wherein the intertwined wires create large interstices in the expandable wire mesh structure, enabling clot penetration of the expandable wire mesh structure.

4. The intraluminal device of claim 1, wherein the flexible shaft includes multiple strands of continuous wire that are coiled, and wherein the expandable wire mesh structure is formed from at least some of the multiple strands.

5. The intraluminal device of claim 4, wherein the multiple strands include wires having differing cross-sectional shapes.

6. The intraluminal device of claim 4, wherein the multiple strands include wires of differing material.

7. The intraluminal device of claim 6, wherein the multiple strands include at least one wire having a radio-opacity that differs from another radio-opacity of at least one other wire.

8. The intraluminal device of claim 1, wherein the expandable wire mesh structure comprises at least one first expandable section having a first wire arrangement pattern and at least one second expandable section having a second wire arrangement pattern different from the first wire arrangement pattern, wherein the first wire arrangement pattern comprises the 1×2 braiding arrangement.

9. The intraluminal device of claim 8, wherein interstices in the at least one first expandable section differ in size from interstices in the at least one second expandable section.

10. An intraluminal device, comprising:
    a flexible shaft;
    an expandable wire mesh structure extending from the flexible shaft, the expandable wire mesh structure including wires comprising a 1×2 braiding arrangement; and
    a control wire extending through the flexible shaft and the expandable wire mesh structure, wherein the expandable wire mesh structure is configured to expand when a force is exerted on the control wire;
    wherein the wires of the expandable wire mesh structure form intertwined wire couples between braided wires of the 1×2 braiding arrangement.

11. The intraluminal device of claim 10, wherein at least a portion of the expandable wire mesh structure comprises alternating braided wires and intertwined wires.

12. The intraluminal device of claim 11, wherein the intertwined wires create large interstices in the expandable wire mesh structure, enabling clot penetration of the expandable wire mesh structure.

13. The intraluminal device of claim 10, wherein the flexible shaft includes multiple strands of continuous wire that are coiled, and wherein the expandable wire mesh structure is formed from at least some of the multiple strands.

14. The intraluminal device of claim 13, wherein the multiple strands include wires having differing cross-sectional shapes.

15. The intraluminal device of claim 13, wherein the multiple strands include wires of differing material.

16. The intraluminal device of claim 15, wherein the multiple strands include at least one wire having a radio-opacity that differs from another radio-opacity of at least one other wire.

17. The intraluminal device of claim 10, wherein the expandable wire mesh structure comprises at least one first expandable section having a first wire arrangement pattern and at least one second expandable section having a second wire arrangement pattern different from the first wire arrangement pattern, wherein the first wire arrangement pattern comprises the 1×2 braiding arrangement.

18. The intraluminal device of claim 17, wherein interstices in the at least one first expandable section differ in size from interstices in the at least one second expandable section.

* * * * *